US00PP19952P2

(12) United States Plant Patent
Lim

(10) Patent No.: US PP19,952 P2
(45) Date of Patent: Apr. 21, 2009

(54) SHRUB ROSE PLANT NAMED 'BAIGIRL'

(50) Latin Name: *Rosa hybrida*
Varietal Denomination: BAIgirl

(75) Inventor: Peter P. Lim, McMinnville, OR (US)

(73) Assignee: Bailey Nurseries, Inc., St. Paul, MN (US)

( * ) Notice: Subject to any disclaimer, the term of this patent is extended or adjusted under 35 U.S.C. 154(b) by 0 days.

(21) Appl. No.: 12/151,415

(22) Filed: May 6, 2008

(51) Int. Cl.
*A01H 5/00* (2006.01)

(52) U.S. Cl. ..... Plt./107

(58) Field of Classification Search ..... Plt./107
See application file for complete search history.

*Primary Examiner*—Annette H Para
*Assistant Examiner*—Georgia Helmer
(74) *Attorney, Agent, or Firm*—Penny J. Aguirre

(57) ABSTRACT

A new cultivar of climbing rose, *Rosa* 'BAIgirl', characterized by its clusters of fully double, ruffled, deep pink flowers that are present in May and June and recurrently throughout the season over medium green, semi-glossy foliage that is resistant to rose blackspot and powdery mildew. The new variety has an upright, compact habit, is readily propagated on its own roots and is hardy in U.S.D.A. Zones 4 to 9.

2 Drawing Sheets

Botanical classification: *Rosa hybrida.*
Variety denomination. 'BAIgirl'.

The present invention relates to a new and distinct cultivar of *Rosa hybrida.* The new cultivar will be referred to hereafter by its cultivar name, 'BAIgirl'. 'BAIgirl' is a shrub rose suitable for landscape plantings.

The new cultivar of shrub rose is a selection from a controlled breeding program conducted by the inventor in Yamhill, Oreg. with a focus to create cultivars of roses with greater winter hardiness and improvements in disease resistance combined with good-flower quality.

The new variety of shrub rose, 'BAIgirl', designated as seedling No. 97R315-1P was selected among seedlings derived from a cross made in Yamhill, Oreg. in 1997 between an unnamed proprietary seedling of the inventor's, No. R92108, as the female parent and 'NOAtraum' (U.S. Plant Pat. No. 7,282) as the male parent. 'BAIgirl' was budded onto understock in 1997 and selected by the inventor as unique for its distinct characteristics in summer of 2000.

The new cultivar has been asexually propagated by budding and rooting of softwood cuttings from a plant grown on its own roots in Yamhill, Oreg. Asexual propagation determined that the characteristics of this cultivar are stable and are reproduced true to type in successive generations.

SUMMARY OF THE INVENTION

The following traits have been repeatedly observed and represent the characteristics of the new rose as observed for a period of seven years in Yamhill, Oreg. St. Paul, Minn. and several other test sites in the U.S. These attributes in combination distinguish 'BAIgirl' as a unique cultivar of shrub rose.

1. 'BAIgirl' exhibits clusters of fully double flowers that are deep pink in color and ruffled. Classified as deep pink by American Rose Society standards.
2. 'BAIgirl' exhibits a compact upright habit with a height of 90 cm to 1.25 m.
3. 'BAIgirl' exhibits medium green, semi-glossy foliage.

4. 'BAIgirl' is a recurrent bloomer.
5. 'BAIgirl' has shown excellent resistance to rose blackspot (*Diplocarpon rosae*) and powdery mildew (*Sphaerotheca pannosa* var. rosa).
6. 'BAIgirl' is hardy in U.S.D.A. Zones 4 to 9.
7. 'BAIgirl' is a vigorous grower and readily propagated by softwood cuttings and grown on its own roots.

The new cultivar of shrub rose can be readily distinguished from its parents and other cultivars. The female parent, seedling No. R92108, is a shrub rose with larger flowers, darker foliage and a less compact habit than 'BAIgirl'. The male parent, 'NOAtraum' is a shrub rose with semi-double flowers and a low spreading plant habit. The cultivars 'Winnipeg Parks' (U.S. Plant Pat. No. 9,122) and 'SPEvu' (U.S. Plant Pat. No. 10,701) are close comparison roses. They both have similarity to 'BAIgirl' in having deep pink flowers and in having compact growth habits. 'Winnipeg Parks' differs from 'BAIgirl' in having flowers that open with a lighter reverse and lack fragrance and in having lighter colored buds, matte foliage, a spreading habit and an everblooming habit. 'SPEvu' differs from 'BAIgirl' in being a polyantha type rose with darker green foliage, a rounded plant habit, flowers that are apple scented, and an everblooming habit.

BRIEF DESCRIPTION OF THE DRAWING

The accompanying colored photographs illustrate the overall appearance and distinct characteristics of the new shrub rose, 'BAIgirl', as grown outdoors in trial blocks and containers in St. Paul, Minn. and Yamhill, Oreg. The photographs were taken of four year-old plants grown on their own roots.

Figure 1:
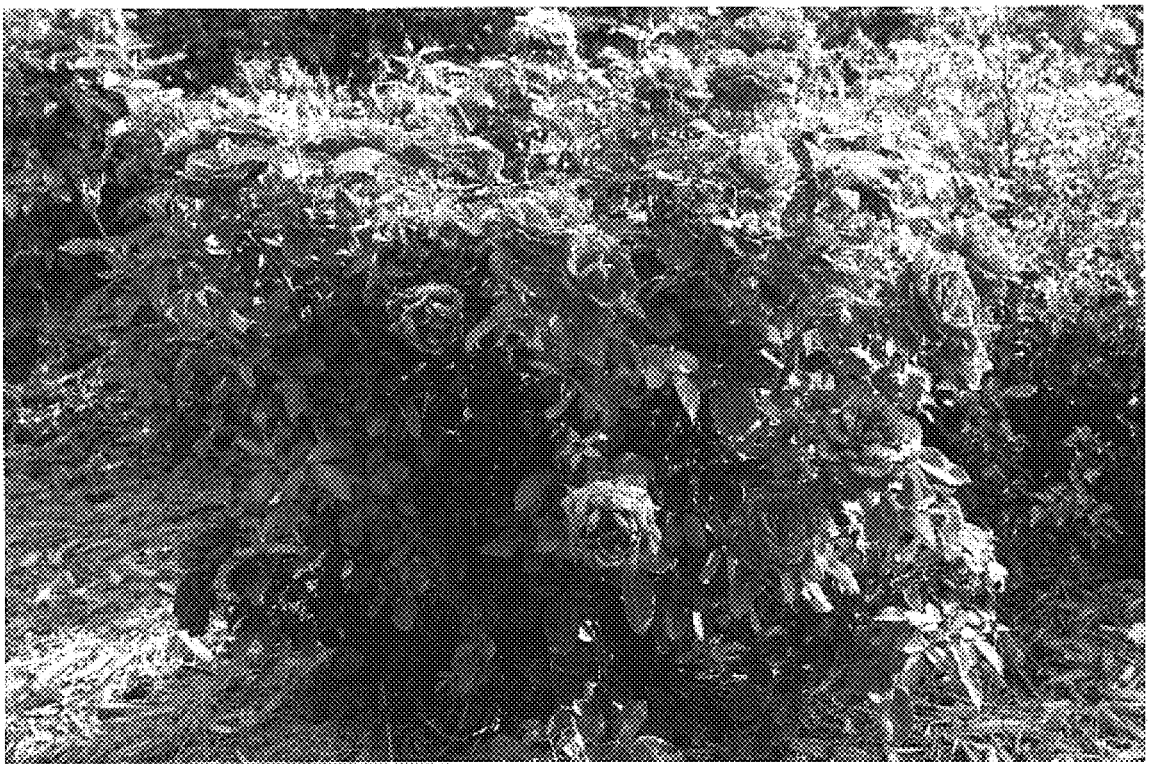
FIG. 1 provides a side view of a plant of 'BAIgirl' in bloom and illustrates its plant habit.
Figure 2:
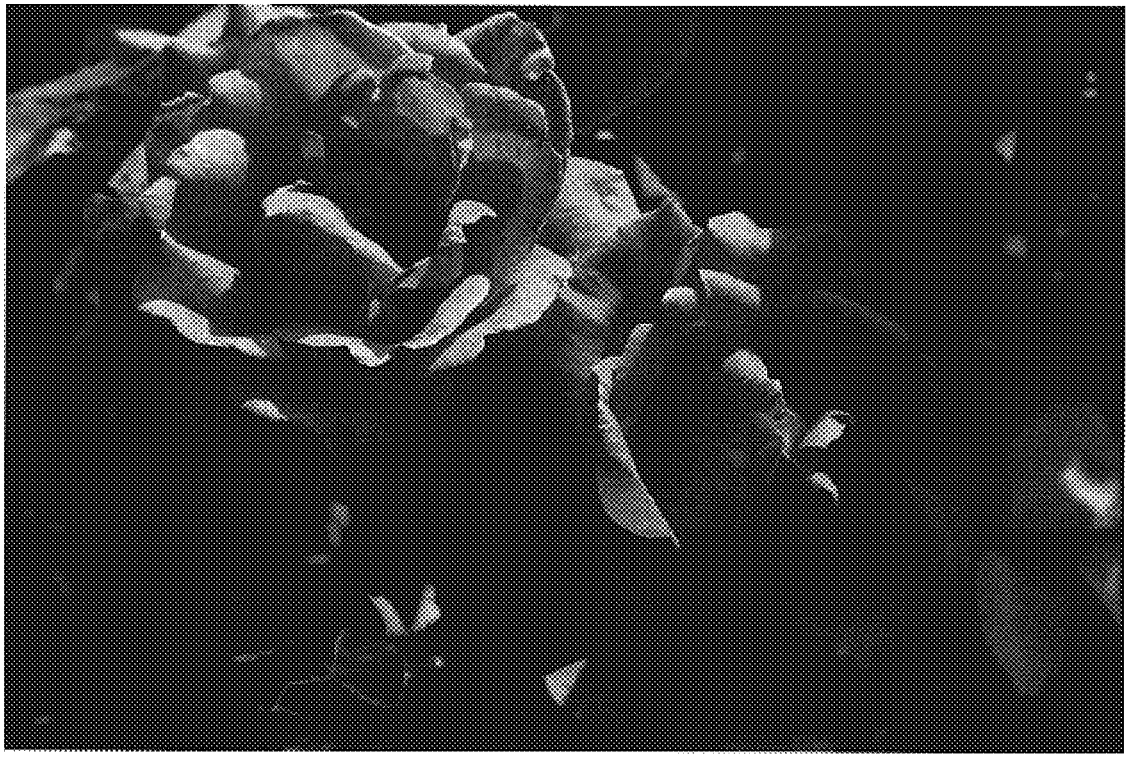
FIG. 2 provides a view of newly opened flowers of 'BAIgirl'.
Figure 3:
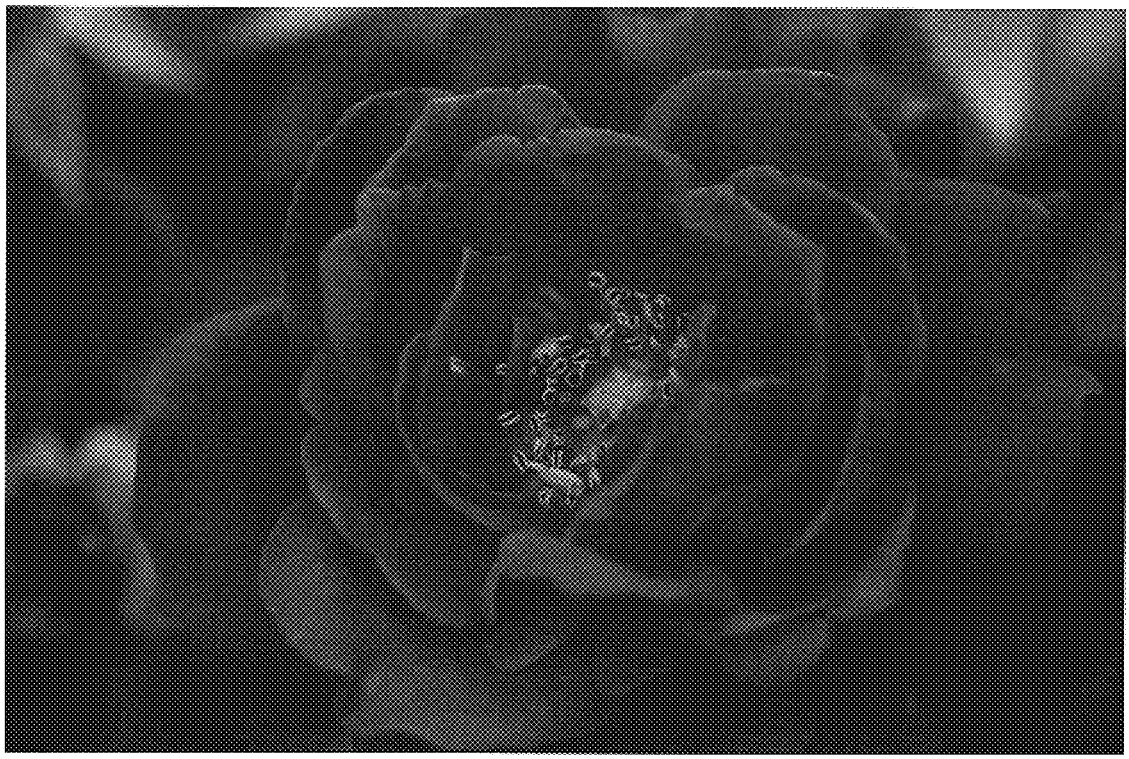
FIG. 3 provides a close-up view of a mature flower of 'BAIgirl'.

The colors in the photographs are as close as possible with digital photography techniques available, the color values cited in the detailed botanical description accurately describe the colors of the new shrub rose.

DETAILED BOTANICAL DESCRIPTION

The following is a detailed description of the new cultivar as observed on two and three year-old container plants and five year-old field-grown plants as grown outdoors in Yamhill, Oreg. and St. Paul, Minn. The phenotype of the new cultivar may vary with variations in environmental, climatic, and cultural conditions, as it has not been tested under all possible environmental conditions. The color determination is in accordance with the 2001 R.H.S. Colour Chart of the Royal Horticultural Society, London, England, except where general color terms of ordinary dictionary significance are used.

General description:

*Blooming habit.*—Abundant in May and June and recurrently throughout the growing season.

*Plant habit.*—Upright and compact.

*Height and spread.*—Reaches 90 cm to 1.25 cm in height and about 1 m in spread.

*Cold hardiness.*—U.S.D.A. Zone 4 to 9.

*Diseases and pests.*—High degree of resistance observed to rose blackspot (*Diplocarpon rosae*) and powdery mildew (*Sphaerotheca pannosa* var. *rosa*).

*Propagation.*—Softwood stem cuttings, own roots.

*Growth.*—Vigorous and strong.

Branch description:

*Stem color.*—Young; 138A, maturing; between 138A and 144A, mature wood; 197B with areas showing through of N138A.

*Stem surface.*—Young and mature; glabrous with abundant thorns, adult wood; mostly glabrous with bark-like ridges.

*Stem size.*—Average of 5 mm in width, up to 1.2 m in length with sub laterals an average of 20 cm in length.

*Thorns.*—Triangular and held horizontal with straight apex, oval base, average of 10 mature thorns per 5 cm in number, an average of 5 mm in length with a base 5 mm in length and 3 mm in width, color is 160A with 199D toward the tip or solid 199D.

*Branching habit.*—About 3 cm internode when lateral branches are formed.

Foliage description:

*Leaves.*—Division is odd-pinnate, average of 19 cm in length and 5 cm in width, internode length is an average of 3 cm.

*Leaflets.*—5 to 7, oval in shape with terminal leaflet more orbicular, rounded to cuneate base, broadly acuminate to nearly cuspidate apex, serrated margins, glabrous and semi-glossy on upper surface and finely puberulent on lower surface, average of 3 cm in length and width for terminal leaflet and 2.7 and 1.8 for lateral leaflets, color: young leaves upper surface; 138A, young leaves lower surface; 138B lightly suffused with 176B, mature leaves upper surface; 137A, mature leaves lower surface; 138A, venation is pinnate, not conspicuous and color of leaflet blade and petiole at base and lower surface midrib.

*Rachis.*—Average of 6.5 cm in length and 1 mm in diameter, color of upper surface 146A and can be suffused with 176B, color of lower surface 144B, surface is glabrous and thorny.

*Stipules.*—Long and narrow with auricle facing outward, adnate to petiole, average of 1.5 cm in length and 6.5 mm in width with leafy apices 5 mm in length and 1 mm in width, color of upper surface is 138A near margin, 144B near center and 144D on middle ridge, color of lower surface is 138A near margin, 144A near center and 144D on middle ridge.

*Petioles.*—Average of 3 mm in length and 1 mm in diameter, color of upper surface 144A, color of lower surface 137B, surface glabrous.

Inflorescence description:

*Inflorescence type.*—Single and in clusters of 2 to 3.

*Flower number.*—Average of 1 to 3 per lateral stem.

*Flower fragrance.*—Light rose scent.

*Flower longevity.*—About 3 to 5 days, depending on temperature and sunlight exposure.

*Flower type.*—Fully double, rosette-shaped.

*Flower size.*—Average of 6.5 cm in diameter (range 5 to 8 cm) and 2.5 cm in depth (to a bottom of sepal tips).

*Flower fragrance.*—Slight rose scent.

*Peduncles.*—Stiff, average of 6 cm in length and 2 mm in diameter, 144A in color, surface is glabrous with prickles and glands.

*Bracts.*—Typically 0 to 1 per flower, if present; average of 2 cm in length and 3 mm in width, lanceolate in shape, sharply serrated margins, apex is acuminate with leaflike tip, truncate base, sessile, color of upper surface 137A with centers on basal region 144A, color of lower surface 137B with centers on basal region 144A.

*Flower buds.*—Ovate in shape, high centered, small to medium in size with an average of 2.3 cm in length and 1.7 cm in diameter prior to opening, blend of 53B to 53D to in color, texture is glabrous and waxy.

*Sepals.*—5, broadly lanceolate in shape, margin is entire on 2 and foliaceous with glandular appendages in irregular or pinnate pattern on 3, color of upper surface is 138A to 138B with margins 196C on non-foliaceous sepals, color of lower surface is 138A with margins 196C on non-foliaceous sepals, upper surface is tomentose, lower surface is rough and glandular, average of 1.5 cm in length and 5 mm in width, apex is apiculate to leaf-like, base is truncate, aspect is upright in bud stage changing to horizontal when bud opens and partially reflexed in full bloom.

*Petals.*—28 to 30, drop readily and cleanly, broadly obovate in shape, upper surface is glabrous and lower surface is glabrous and satiny, margin is ruffled with occasional crenations, cuneate base, rounded apex, average of 2.2 cm in length and 2.2 cm in width, color: opening flowers upper surface; blend of N57B and 63B, opening flowers lower surface; 63B suffused with 63C to 63D, fully open flowers upper surface; blend of N57B and 63B, fully open flowers lower surface; 63B suffused with 63C to 63D, end of bloom upper surface; 68B suffused with 68A, end of bloom lower surface; blend of 63C and 63D, both surfaces dry to N79C just before drop, petal spot; 155C with 8D at tip of base.

*Receptacle.*—Average of 5 mm in diameter and 4 mm in depth when flower is fully open, vase-shaped, glabrous and satiny, 144A in color.

*Pistils.*—About 38, stigma is an average of 0.4 mm in length and 0.3 mm width and 1C in color, style is an average of 5 cm in length and 155A in color with shadings of 63B, ovary is 2 mm in length and 1 mm width, 155A in color and pilose with very fine hairs about 2 mm in length.

*Stamens.*—About 90 with occasional petaloid stamens, held upright, filaments are an average of 6 mm in length and 22B in color with a slight cast of 63D, anthers are an average of 0.7 mm in length and width, basifixed, held downward, and 200C in color, pollen is abundant in quantity and 22A in color.

*Hips.*—Round in shape, medium small in size with an average of 1.3 mm in length and diameter, surface is glabrous and shiny, color is 170A when mature, seeds; average of 6 per hip, kernel to flattened in shape, an average of 4 mm and width, surface is rugose at apex with villose hairs.

It is claimed:

1. A new and distinct cultivar of climbing rose plant named 'BaIgirl' as herein illustrated and described.

* * * * *